US008641596B2

(12) United States Patent
Meskens

(10) Patent No.: US 8,641,596 B2
(45) Date of Patent: Feb. 4, 2014

(54) WIRELESS COMMUNICATION IN A MULTIMODAL AUDITORY PROSTHESIS

(75) Inventor: Werner Meskens, Opwijk (BE)

(73) Assignee: Cochlear Limited, Macquarie University, NSW (AU)

(*) Notice: Subject to any disclaimer, the term of this patent is extended or adjusted under 35 U.S.C. 154(b) by 746 days.

(21) Appl. No.: 12/497,144

(22) Filed: Jul. 2, 2009

(65) Prior Publication Data

US 2010/0030012 A1    Feb. 4, 2010

(30) Foreign Application Priority Data

Jul. 2, 2008  (AU) ................................ 2008903416

(51) Int. Cl.
*A61F 11/04* (2006.01)
(52) U.S. Cl.
USPC ............................................................ 600/25
(58) Field of Classification Search
USPC ......... 600/25; 607/55–57; 381/312–331, 150, 381/151
See application file for complete search history.

(56) References Cited

U.S. PATENT DOCUMENTS

| 5,176,620 | A | * | 1/1993 | Gilman ............................ 600/25 |
| 5,606,621 | A | | 2/1997 | Reiter et al. |
| 5,721,783 | A | * | 2/1998 | Anderson ..................... 381/328 |
| 5,793,875 | A | | 8/1998 | Lehr et al. |
| 5,800,336 | A | * | 9/1998 | Ball et al. ........................ 600/25 |
| 6,231,604 | B1 | | 5/2001 | von Ilberg |
| 6,556,870 | B2 | | 4/2003 | Zierhofer et al. |
| 7,139,404 | B2 | | 11/2006 | Feeley et al. |
| 2002/0012438 | A1 | | 1/2002 | Leysieffer et al. |
| 2002/0071581 | A1 | | 6/2002 | Leysieffer et al. |
| 2004/0202339 | A1 | * | 10/2004 | O'Brien et al. ............... 381/312 |
| 2006/0233409 | A1 | | 10/2006 | Weidner |
| 2008/0123866 | A1 | * | 5/2008 | Rule et al. .................... 381/71.6 |

FOREIGN PATENT DOCUMENTS

| EP | 1017252 A2 | 7/2000 |
| WO | 98/26629 | 6/1998 |

OTHER PUBLICATIONS

European Search Report and Search Opinion for European Application No. 09163838.7 mailed Dec. 5, 2012 (6 pages).

* cited by examiner

*Primary Examiner* — Christine Matthews
*Assistant Examiner* — Joshua D Lannau
(74) *Attorney, Agent, or Firm* — Kilpatrick, Townsend & Stockton, LLP.

(57) ABSTRACT

A multimodal auditory prosthesis. The prosthesis comprises a sound processing unit configured to process sound and to generate electrical signals representing different frequency components of the processed sound and a stimulation module communicably coupled to the sound processing unit, configured to stimulate the recipient to evoke a hearing percept of a range of the frequency components. The prosthesis also comprises an external stimulation module, configured to be positioned within an externally accessible portion of the recipient's first ear, comprising: a receiver unit to wirelessly receive the electrical signals representing the different frequency components, and a transducer that delivers acoustic or mechanical energy to the recipient's ear to evoke a hearing percept of a range of the frequency components.

32 Claims, 9 Drawing Sheets

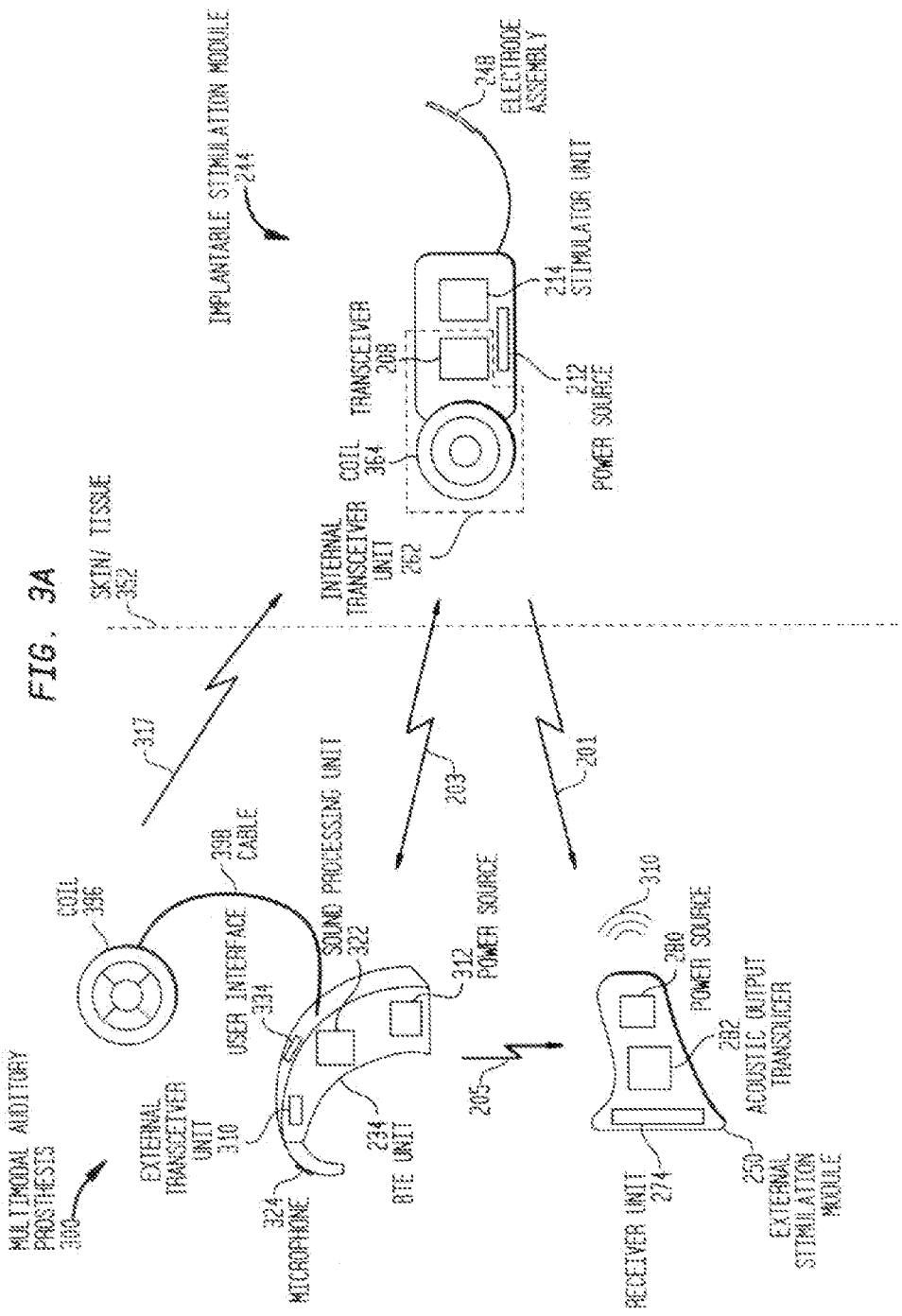

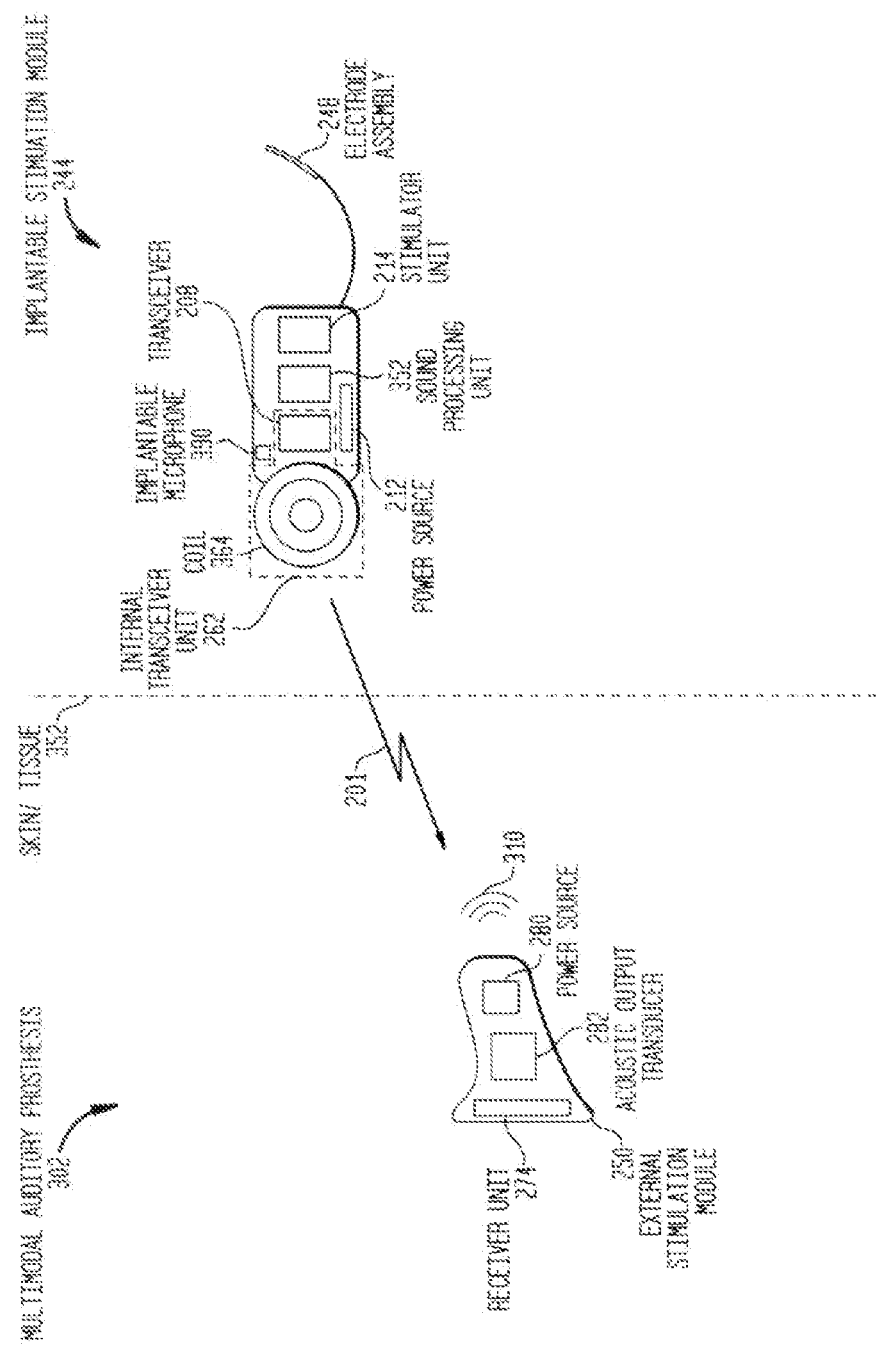

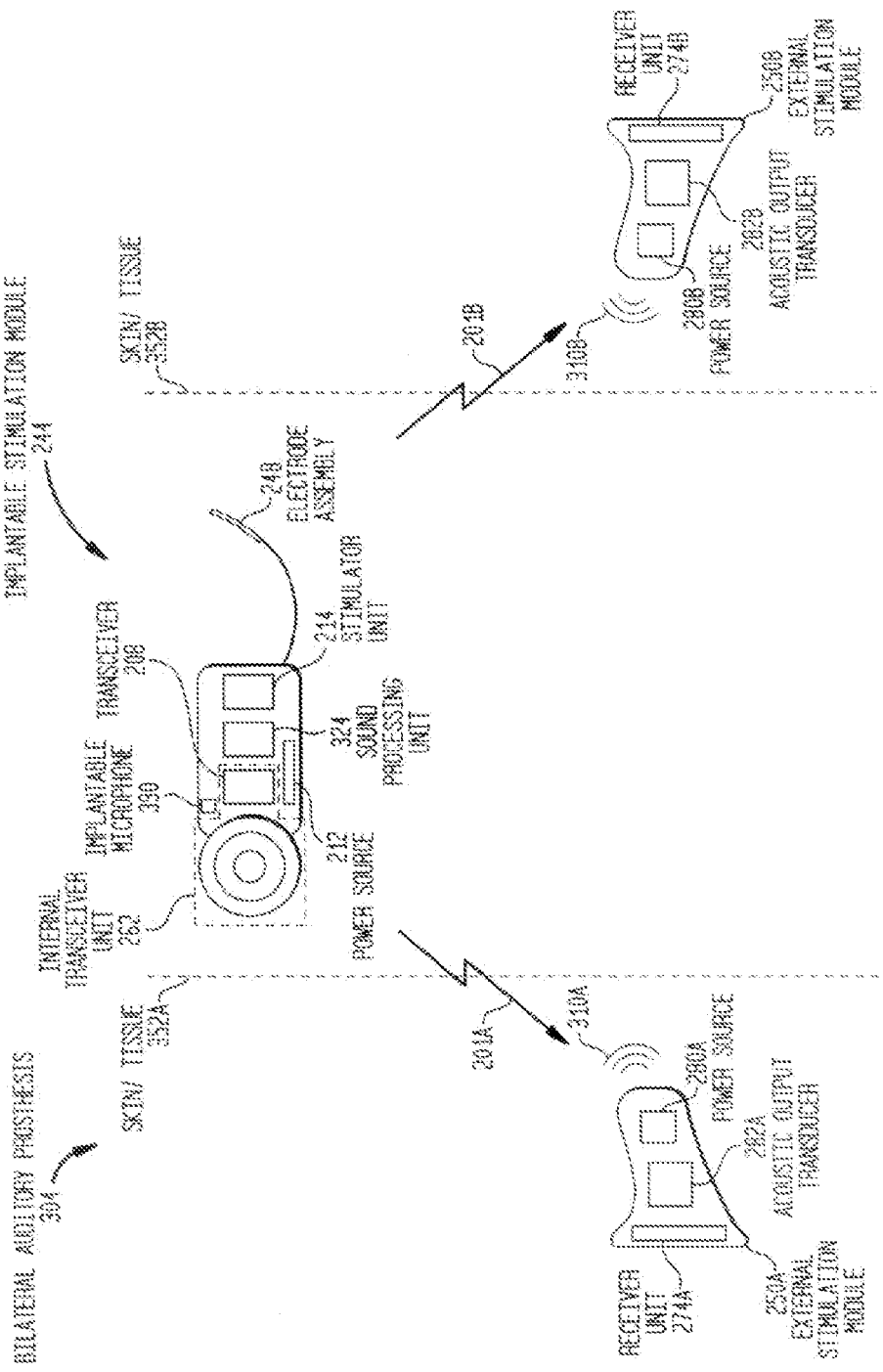

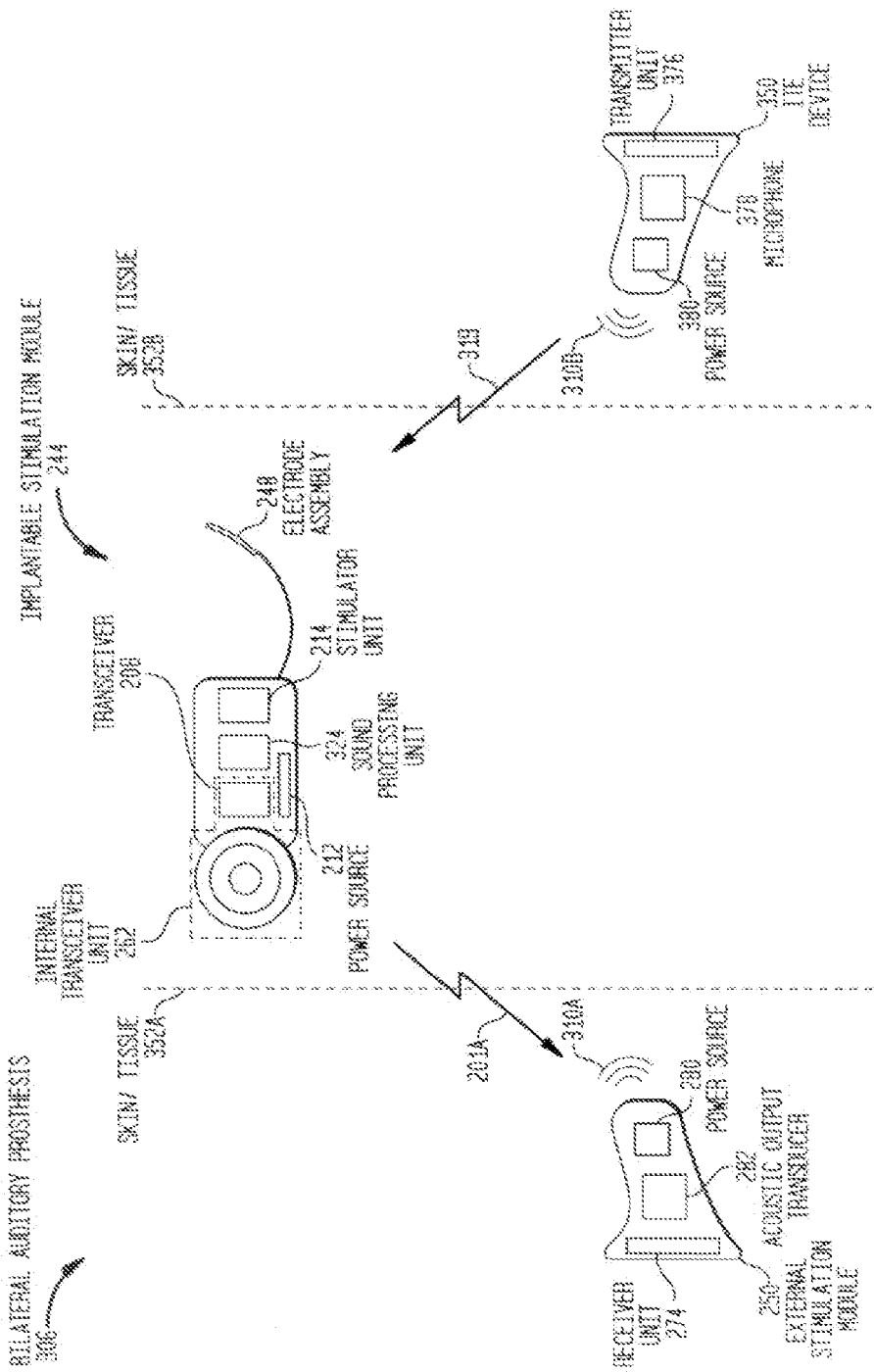

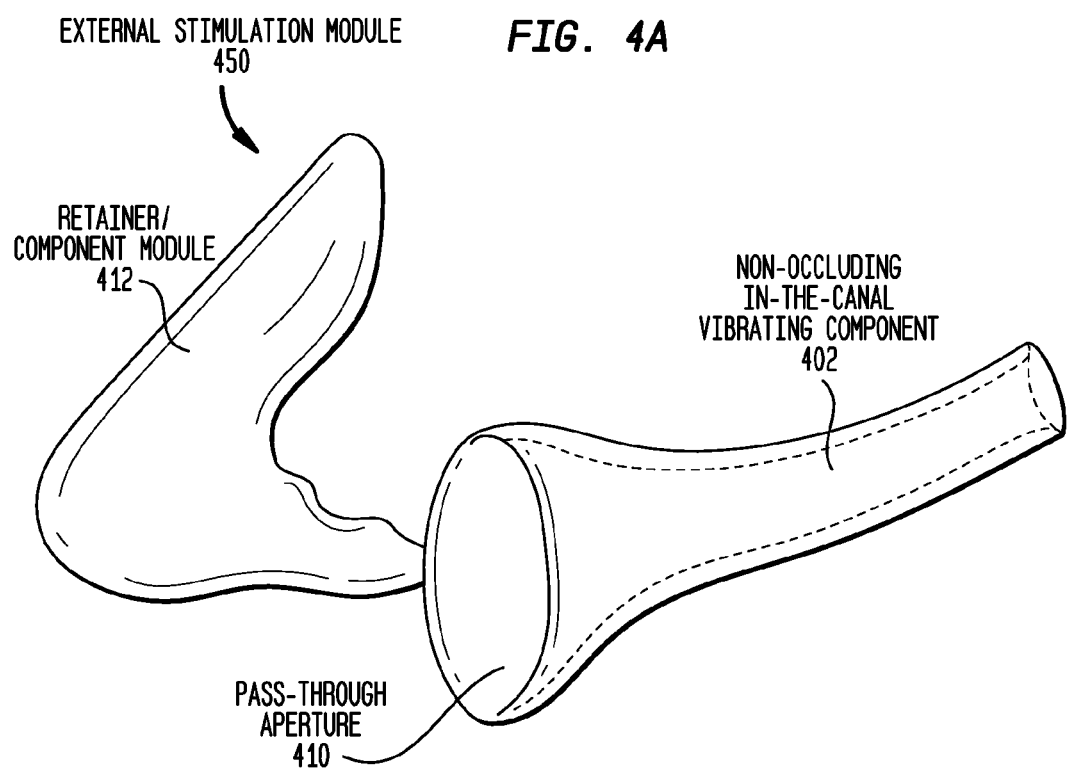

WIRELESS COMMUNICATION IN A MULTIMODAL AUDITORY PROSTHESIS

CROSS-REFERENCE TO RELATED APPLICATIONS

The present invention claims the benefit of Australian Provisional Application No. 2008903416; filed Jul. 2, 2008. The content of this application is hereby incorporated by reference herein.

BACKGROUND

1. Field of the Invention

The present invention relates generally to multimodal auditory prostheses and, more particularly, to wireless communication in a multimodal auditory prosthesis.

2. Related Art

Hearing loss is generally of two types, namely conductive and sensorineural. Conductive hearing loss occurs when the normal mechanical pathways that provide sound to hair cells in the cochlea are impeded, for example, by damage to the ossicular chain or to the ear canal. Individuals suffering from conductive hearing loss typically have some form of residual hearing because the hair cells in the cochlea are undamaged. As a result, such individuals typically receive an auditory prosthesis that delivers acoustic or mechanical energy to the ear. For example, acoustic energy may be delivered through a column of air to the tympanic membrane (eardrum) via a hearing aid residing in the ear canal. Mechanical energy may be delivered via the physical coupling of a mechanical transducer (i.e. a transducer that converts electrical signals to mechanical motion) to the tympanic membrane, the skull, the ossicular chain, the round or oval window of the cochlea or other structure that will result in the application of the imposed mechanical energy to the hydro-mechanical system of the cochlea.

Sensorineural hearing loss occurs when there is damage to the inner ear, or to the nerve pathways from the cochlea to the brain. As such, those suffering from sensorineural hearing loss are thus unable to derive suitable benefit from auditory prostheses that deliver acoustic or mechanical energy. As a result, auditory prostheses that electrical stimulation signals to nerve cells of the recipient's auditory system have been developed to provide such individuals with the ability to perceive sound.

For example, cochlear implants are generally recommended when the sensorineural hearing loss is due to the absence or destruction of the cochlea hair cells which transduce acoustic signals into nerve impulses. Cochlear implants electrically stimulate a recipient's cochlea by directly delivering direct electrical stimulation signals to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

In circumstances in which the electrical impulses generated by the cochlea are not delivered to the brain due to disease, injury or absence of the spiral ganglion cells or auditory nerve, another type of electrically-stimulating hearing prosthesis referred to as an auditory brain implant (ABI) is generally recommended. ABIs provide electrical stimulation directly to the auditory cortex of the brain via an array of electrodes.

As noted, the treatment of both conductive and sensorineural hearing loss has been quite different, relying on two different principles to deliver sound signals to be perceived by the brain as sound. Furthermore, it is relatively common in hearing impaired individuals to experience severe sensorineural hearing loss for sounds in the high frequency range, and yet still be able to discern sounds in the middle to low frequency range. Traditionally, such recipients receive treatment to preserve and/or improve perception of the middle to low frequency sounds using, for example, an auditory prosthesis that delivers acoustic or mechanical stimulation, and little is done to restore the severe hearing loss of high frequency sounds.

More recently, there has been an increased interest in multimodal auditory prostheses that are capable of using multiple types of stimulation to stimulate a recipient's ear. Using multiple types of stimulation provides a recipient with the ability to perceive a wider range of frequencies regardless of the cause of hearing loss. One exemplary type of multimodal prosthesis utilizes electrical and acoustical stimulation, commonly referred to as an Electro-Acoustical Stimulation (EAS) device. In EAS devices, acoustic stimulation is used to amplify the low frequencies of the received sound while electrical stimulation is used to provide the recipient with the ability to perceive middle and high frequencies of the sound.

SUMMARY

In one aspect of the present invention, an auditory prosthesis is provided. The auditory prosthesis comprises: a sound processing unit configured to process sound and to generate electrical signals representing different frequency components of the processed sound; a stimulation module communicably coupled to the sound processing unit, configured to stimulate the recipient to evoke a hearing percept of a range of the frequency components; and an external stimulation module, configured to be positioned within an externally accessible portion of the recipient's ear, comprising: a receiver unit to wirelessly receive the electrical signals representing the different frequency components, and a transducer that delivers acoustic or mechanical energy to the recipient's ear to evoke a hearing percept of a range of the frequency components.

In another aspect of the present invention, a bilateral auditory prosthesis is provided. The prosthesis comprises: a sound processing unit configured to process sound and to generate electrical signals representing different frequency components of the processed sound; a stimulation module communicably coupled to the sound processing unit, configured to stimulate the recipient to evoke a hearing percept of a range of the frequency components; an external stimulation module, configured to be positioned within an externally accessible portion of the recipient's first ear and comprising: a receiver unit to wirelessly receive the electrical signals representing the different frequency components, and a transducer that delivers acoustic or mechanical energy to the recipient's ear to evoke a hearing percept of a range of the frequency components; and an external device, configured to be positioned within an externally accessible portion of the recipient's second ear, and configured to wirelessly communicate with one or more of the stimulation module and the sound processing unit.

BRIEF DESCRIPTION OF THE DRAWINGS

Embodiments of the present invention are described below with reference to the attached drawings, in which:

FIG. 3A is a schematic diagram of a multimodal auditory prosthesis in accordance with embodiments of the present invention;

FIG. 3B is a schematic diagram of a multimodal auditory prosthesis in accordance with embodiments of the present invention;

FIG. 3C is a schematic diagram of a multimodal auditory prosthesis in accordance with embodiments of the present invention;

FIG. 3D is a schematic diagram of a multimodal auditory prosthesis in accordance with embodiments of the present invention;

FIG. 4A is a perspective view of an external stimulation module in accordance with embodiments of the present invention.

DETAILED DESCRIPTION

Aspects of the present invention are generally directed to wireless communication in a multimodal auditory prosthesis. The multimodal auditory prosthesis comprises a sound processing unit configured to process sound and to generate electrical signals representing different frequency components of the processed sound. A stimulation module is communicably coupled to the sound processing unit and is configured to stimulate the recipient to evoke a hearing percept of a range of the frequency components. The prosthesis also comprises an external stimulation module that is configured to be positioned within an externally accessible portion of the recipient's ear. The external stimulation module comprises a receiver unit to wirelessly receive electrical signals representing frequency components of the processed sound, and a transducer that delivers acoustic or mechanical energy to the recipient's ear to evoke a hearing percept of a range of the frequency components of the processed sound.

In certain embodiments of the present invention, the stimulation module is implantable within the recipient. In certain such embodiments, the implantable stimulation module further comprises the sound processing unit and a transceiver unit which wirelessly transmits the electrical signals representing the different frequency components to the external stimulation module.

In other embodiments of the present invention, the sound processing unit is disposed in an external component such as, for example, a behind-the-ear (BTE) unit or a body worn unit. In such embodiments, the external component comprises a transceiver unit configured to wirelessly provide the electrical signals representing the different frequency components to the external stimulation module.

Embodiments of the present invention are described herein primarily in connection with one type of multimodal hearing prosthesis, namely an auditory prosthesis that delivers electro-acoustic stimulation (EAS). Such EAS devices include components of a cochlear prosthesis (commonly referred to as a cochlear prosthetic device, cochlear implant, cochlear device, and the like; simply "cochlear implants" herein) which deliver electrical stimulation signals to a recipient's cochlea, and components which deliver acoustic or mechanical energy to the recipient's ear to generate motion of the recipient's inner ear fluid. As described in greater detail below, it would be appreciated that embodiments of the present invention may be implemented in any partially or fully implantable multimodal prosthesis now known or later developed, including, but not limited to, prostheses that include components of bone conduction devices, auditory brain stimulators, middle ear mechanical stimulators, or other prostheses that electrically, acoustically and/or mechanically stimulate the recipient to evoke a hearing percept.

Figure 1:
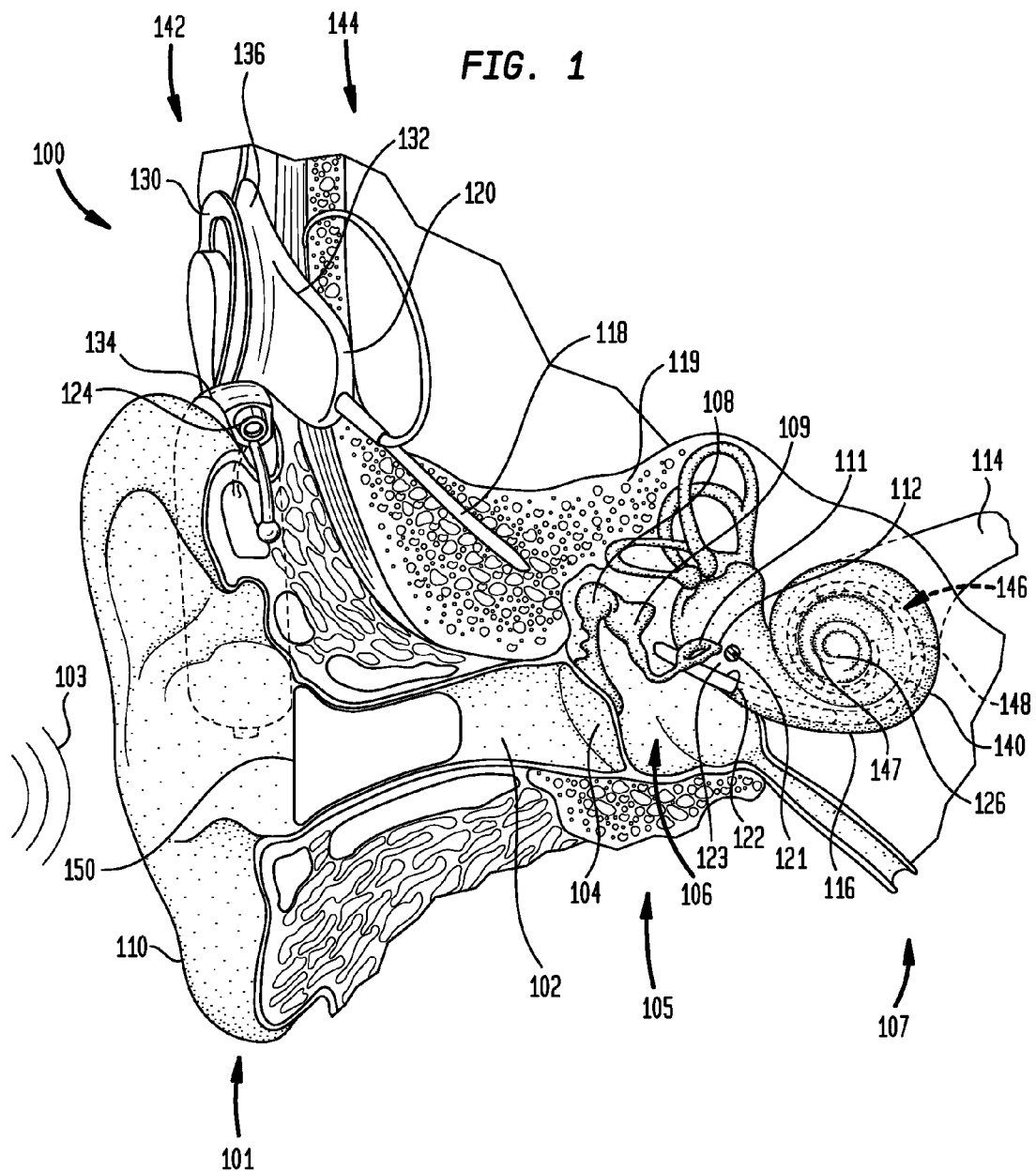
FIG. 1 is a perspective view of an exemplary multimodal auditory prosthesis, in which embodiments of the present invention may be implemented.

FIG. 1 is perspective view of a multimodal auditory prosthesis 100 implanted in a recipient. The recipient has an outer ear 101, a middle ear 105 and an inner ear 107. Components of outer ear 101, middle ear 105 and inner ear 107 are described below, followed by a description of auditory prosthesis 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, auditory prosthesis 100 comprises an external component 142 which is directly or indirectly attached to the body of the recipient, and an internal or implantable stimulation module 144 which is temporarily or permanently implanted in the recipient. External component 142 may comprise one or more functional components which generate to receive data. In the exemplary arrangement of FIG. 1, external component 142 comprises a behind-the-ear (BTE) unit 134 having one or more sound input elements 124 for detecting sound. It would be appreciated that sound input elements 124 may comprise, for example, a microphone or an electrical input configured to connect prosthesis 100 to external equipment and receive an electrical sound signal directly there from. For example, an electrical input may permit prosthesis to be connected to, FM hearing systems, MP3 players, televisions, mobile phones, etc. For ease of illustration, embodiments of the present invention will be described herein with reference to a microphone as the sound input element.

Microphone 124 converts the detected sound into electrical signals. Disposed in BTE unit 134 is a sound processing unit (not shown) that converts the microphone output electrical signals representing different frequency components of the detected sound. As described in detail below, BTE 134 may comprise a transceiver unit which transmits these electrical signals to one or more other components.

In the embodiments of FIG. 1, BTE unit 134 wirelessly transmits the electrical signals output by the sound processing unit to an internal transceiver unit 132 in internal component 144. Transceiver unit 132 may be positioned in a recess of the temporal bone adjacent auricle 110 of the recipient. Transceiver unit 132 transcutaneously receives power and data signals from external component 142 using one or more types of wireless transmission. For example, in certain embodiments, radio frequency (RF) links may be used to transmit power and data to transceiver unit 132. In such embodiments, transceiver unit 132 comprises an internal coil 136, a magnet (also not shown) fixed relative to the internal coil. Internal coil 136 is typically a wire antenna coil comprised of multiple turns of electrically insulated single-strand or multi-strand platinum or gold wire. As would be appreciated, transceiver unit 132 may also transmit data signals to external component 142. For example, data signals transmitted by transceiver unit 132 may be received by the transceiver unit in BTE 134.

Implantable stimulation module 144 further comprises a power source (not shown) for storing power delivered from external component 142, a stimulator unit 120 and an elongate electrode assembly 118. Internal transceiver unit 132 and stimulator unit 120 are hermetically sealed within a biocompatible housing, sometimes collectively referred to as a main module 120. Elongate electrode assembly 118 has a proximal end connected to main module 120, and a distal end implanted in cochlea 140. Electrode assembly 118 extends from main module 120 to cochlea 140 through mastoid bone 119. Electrode assembly 118 is inserted or implanted into cochlea 140. In some embodiments electrode assembly 118 may be implanted at least in basal region 116, and sometimes further. For example, electrode assembly 118 may extend towards apical end of cochlea 140, referred to as cochlea apex 126. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140. In certain embodiments, an additional electrode assembly may be provided. This electrode assembly can be mounted within, or external to, the cochlea of the recipient.

As is known, electrode assembly 118 may be implanted in cochlea 140 without damaging the recipient's residual hearing. That is, implantation of electrode assembly 118 into cochlea 140 does not significantly damage the remaining hair cell population, nor does it interfere with the cochlea fluid mechanics.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals based on data signals received from BTE 134, which are applied by electrodes 148 to cochlea 140, thereby stimulating auditory nerve 114 and evoking a hearing percept. Stimulator 120 and electrode assembly 118 collectively comprise an implantable stimulation module.

In the embodiments of FIG. 1, auditory prosthesis further comprises an external stimulation module 150 that is non-surgically positioned within the externally accessible portion of the recipient's ear. In certain embodiments, external stimulation module 150 may comprise an in-the-ear (ITE) unit that fits within the ear bowl. Certain such devices are sometimes referred to as full shell or half shell devices. In alternative embodiments, external stimulation module 150 may comprise a completely-in-canal (CIC) unit that is shaped to fit into the recipient's ear canal such that the unit contacts the bony portion of the ear canal. In another embodiment, external stimulation module 150 may comprise an in-the-canal (ITC) unit that is positionable just outside the ear canal. In yet another embodiment, ITE unit 150 may comprise a microcanal (MIC) unit that is slightly smaller in size than the ITC unit.

As detailed below, external stimulation module 150 comprises a receiver unit (not shown) that wirelessly receives the electrical signals representing the different frequency components of the detected sound signal. External stimulation module 150 also includes an output transducer (also not shown) that stimulates the recipient's ear based on the received electrical signals. Thus, the output transducer evokes a hearing percept of a frequency range of the detected sound. In embodiments of FIG. 1, the output transducer provides acoustic stimulation signals (sound waves) to the tympanic membrane 104 which vibrates in response to the acoustic stimulation signals. This vibration is coupled to the inner ear fluid via the bones of middle ear 105, thereby activating the cochlea hair cells.

As noted above, multimodal auditory prosthesis 100 delivers acoustic and electrical stimulation signals to the recipient's ear. In certain embodiments, the acoustic and electrical stimulation signals are each delivered to cause perception of different frequency ranges of the detected sound. For example, it is known that the cochlea is tonotopically mapped. That is, certain regions of the cochlea, namely basal region 116, is responsive to high frequency signals while regions of the cochlea approaching apex 126 are responsive to increasingly lower frequency signals. Therefore, in certain embodiments of the present invention, electrode assembly 118 delivers electrical signals to basal region 116 to cause the recipient to perceive high frequency signals, while external stimulation module 150 delivers acoustic signals that evoke perception of lower frequency sounds.

In the embodiments of FIG. 1, auditory prosthesis 100 comprises external component 142 that includes BTE 134. It should be appreciated that in alternative embodiments external component 142 may comprise a body worn unit, a pinna attached unit, etc., instead or, or in addition to, BTE 134. In further embodiments, external component 142 may be fully or partially omitted. In such embodiments, implantable stimulation module 144 is capable of operating, at least for a period of time, without the need for an external device.

As noted, implantable stimulation module 144 further comprises a power source (not shown) that stores power received from an external device. The power source may comprise, for example, a rechargeable battery. During operation of implantable stimulation module 144, the power stored by the power source is distributed to the various other implanted components as needed. The power source may be located in the main module 120, or disposed in a separate implanted location.

Embodiments of the present invention are primarily described herein with reference to an implantable stimulation module. However, it should be appreciated that in certain embodiments, the stimulation module may be positioned external to the recipient. For example in certain embodiments, a stimulation module that delivers vibration to the recipient's skull to evoke a hearing percept via bone conduction may be utilized. Such a stimulation module may be external to the recipient, or, in certain circumstances, implantable.

Figure 2A:
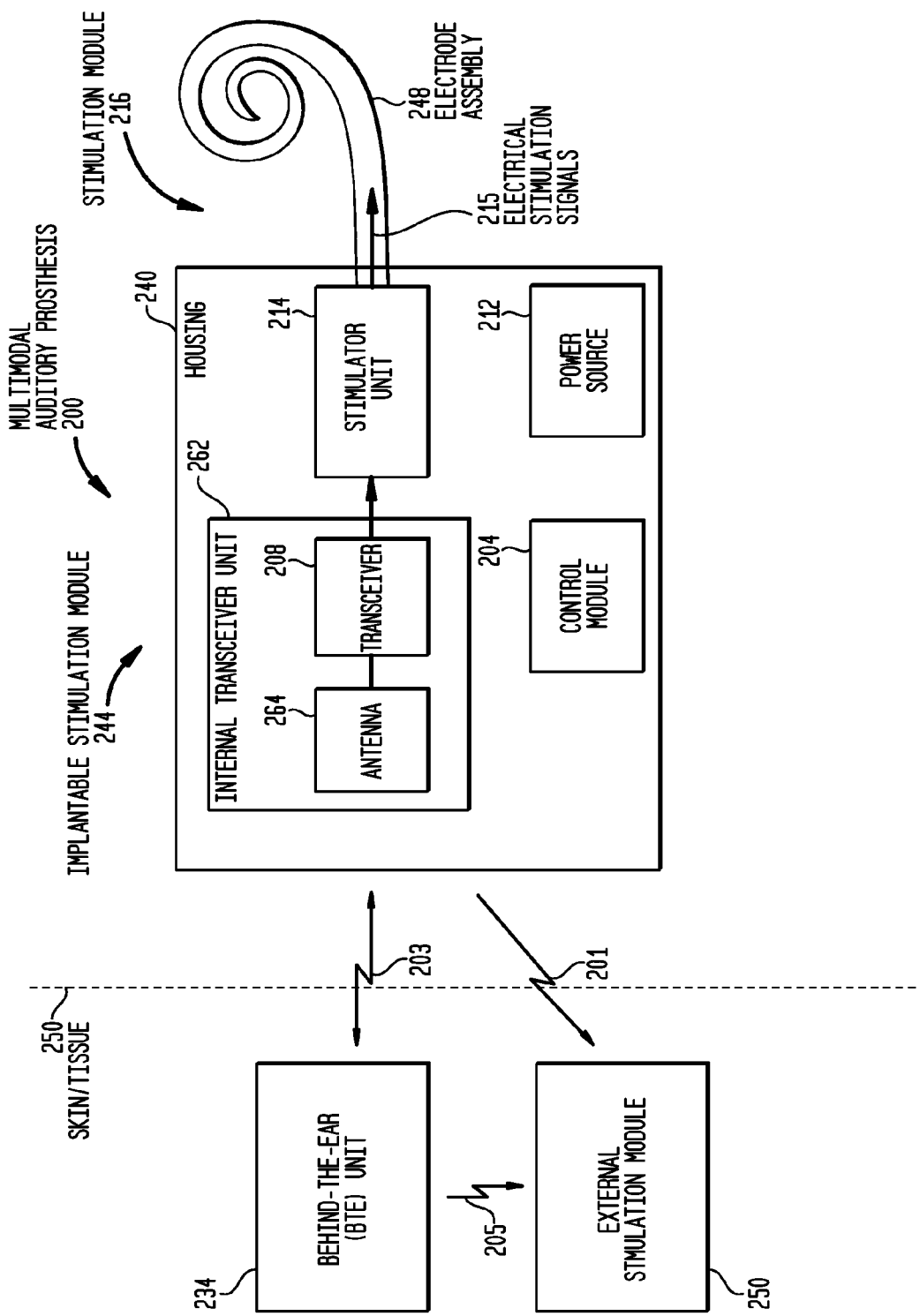
FIG. 2A is a functional block diagram of a multimodal auditory prosthesis in accordance with embodiments of the present invention.

FIG. 2A is a functional block diagram of a multimodal auditory prosthesis 200 in accordance with embodiments of the present invention. Auditory prosthesis 200 comprises an implantable stimulation module 244 which, similar to implantable stimulation module 144 of FIG. 1, is configured to be implanted beneath a recipient's skin or other tissue to stimulate the recipient's ear.

In the embodiments of FIG. 2A, auditory prosthesis 200 comprises a behind-the-ear (BTE) unit 234 which is similar to BTE 134 of FIG. 1. Implantable stimulation module 244 comprises an internal transceiver unit 262 which, in this embodiment, receives data and power signals from BTE 234. More specifically, internal transceiver unit 262 comprises an antenna 264 for receiving and/or transmitting signals, and a transceiver 208. Transceiver 208 comprises one or more circuit elements that decode signals received by antenna 264. Antenna 264 may comprise, for example, a coil for a magnetic inductive arrangement, an antenna for an alternative RF system, components of an optical transmission system, capacitive plates, or any other suitable arrangement used to form a wireless communication link. As such, in embodiments of the present invention, various types of energy transfer, such as infrared (IR), electromagnetic, capacitive and inductive transfer, may be used to transfer the power and/or data from BTE 234 to implantable stimulation module 244.

As shown, implantable stimulation module 244 includes a housing 240 having internal transceiver unit 262 hermetically sealed with a power storage element, shown as power source 212, a control module 204, a stimulator unit 214. Extending from housing 240 is an electrode assembly 248. Power source 212 is configured to store power received by transceiver unit 262, and to distribute power, as needed, to the elements of implantable stimulation module 244. Power source 212 may comprise, for example, a rechargeable battery 212.

In the embodiments of FIG. 2A, electrical signals representative of a detected sound signal are transmitted from BTE unit 234 to transceiver unit 262 where the signals are provided to stimulator unit 214. Based on the received signals, stimulator unit 214 generates electrical stimulation signals 215 for delivery to the cochlea of the recipient. In the embodiment illustrated in FIG. 2A, implantable stimulation module 244 comprises an embodiment of electrode assembly 118 of FIG. 1, referred to as electrode assembly 248, for delivering stimulation signal 215 to the cochlea.

As shown in FIG. 2A, communication link 203 is a bi-directional communication link. As such, transceiver unit 262 may be configured to transmit data signals over link 203 to BTE unit 234.

Multimodal auditory prosthesis 200 further comprises an external stimulation module 250 which is similar to external stimulation module 150 of FIG. 1. As described in greater detail below, external stimulation module 250 is configured to wirelessly receive electrical signals representing a detected sound signal from BTE unit 234 or from implantable stimulation module 244. Therefore, external stimulation module 250 is entirely physically and electrically isolated from the other components, and no external connecting wires are required.

As such, wireless communication links 205 and 201 are provided between external stimulation module 250 and BTE unit 234 and implantable stimulation module 244, respectively. Similar to link 203 described above, links 201 and 205 may comprise electromagnetic induction links, RF links, capacitive links or any other suitable wireless communication link. Similarly, links 201 and 205 may comprise the same or different type of communication link. It would be appreciated that, depending on the desired device configuration, one of links 201 and 205 may be omitted.

Figure 2B:
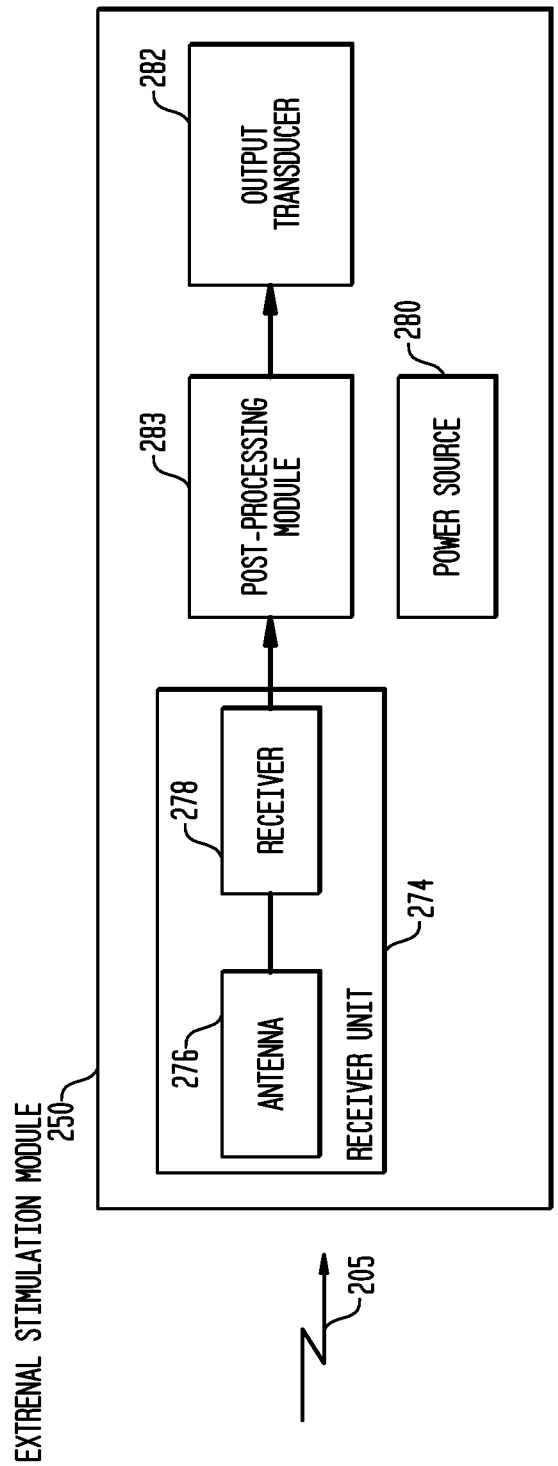
FIG. 2B is a functional block diagram of the external stimulation module of FIG. 2A.

FIG. 2B is a functional block diagram illustrating external stimulation module 250 in more detail. In the embodiments of FIG. 2B, external stimulation module 250 comprises a receiver unit 274 that receives data signals from BTE 234 and/or implantable stimulation module 244 via wireless communication links 205 and 201, respectively. The embodiments of FIG. 2B will be described with reference to data signals received from BTE 234 via communication link 205. For ease of illustration, communication link 201 has been omitted from FIG. 2B.

Data signals transmitted via communication link 205 are received by antenna 276 in receiver unit 274. As noted, link 205 may comprise a number of different types of links. Therefore, antenna 264 may comprise, for example a coil for a magnetic inductive arrangement, an antenna for an alternative RF system, components of an optical transmission system, capacitive plates, or any other suitable arrangement used to form a wireless communication link. Also as noted, links 201 and 205 may be the same or different types of links. In embodiments in which different types of links are used, receiver unit 274 may comprise multiple antennas and other components for use with the different types of links. Receiver unit 274 further comprises one or more circuit elements that decode signals received by antenna 264, referred to as receiver 278.

Figure 4B:
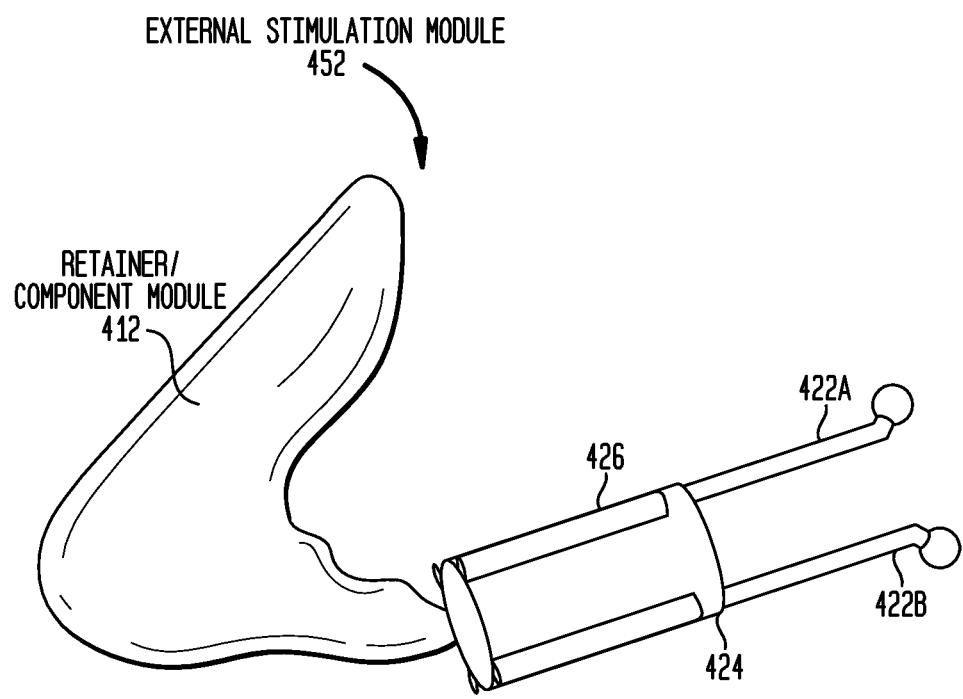
FIG. 4B is a perspective view of an external stimulation module in accordance with embodiments of the present invention.

The data signals received by receiver unit 274 are provided to post-processing module 283. Post-processing module 283 processes and responses the received data for use by an output transducer 282 for generating stimulation signals for delivery to the recipient. Output transducer 282 is configured to generate acoustic or mechanical stimulation signals which, when delivered to the recipient, evoke a hearing percept of frequency components of sound detected by a sound input element located elsewhere in auditory prosthesis 200. In embodiments in which acoustical stimulation signals are desired, output transducer 282 comprises an acoustic transducer, such as a loudspeaker, that generates sound waves. The embodiments of FIGS. 3A-3D are described with reference to the use of an acoustic output transducer. However, FIGS. 4A and 4B illustrate exemplary external stimulation modules having mechanical output transducers that deliver mechanical stimulation signals to the recipient.

As noted, in embodiments of the present invention BTE unit 234 wirelessly transmits electrical signals representing frequency components of a processed sound to external stimulation module 250 and to implantable stimulation module 244. In certain such embodiments, the wireless data signals provided to modules 250 and 244 each include the full range of audio frequencies. Furthermore, the wireless data is digitally compressed by adapted vocal or musical algorithms. Therefore, modules 250 and 244 are not responsive to specific or small ranges of frequencies because the entire range of frequencies are provided to the modules. In further embodiments, the wireless data signals have a constant compressed data rate. A constant data or symbol rate at wireless link level allows using a common radio front-end structure, and is advantageous for low-latency compression/decompression schemes. This also helps to avoid having unbalanced streams between left and right devices in bilateral systems, required for beam forming and localization algorithms.

As shown in FIG. 2B, external stimulation module 250 comprises a power storage element, shown as power source 280. Power source 280 may comprise, for example, a rechargeable battery 280. In certain embodiments of the present invention, receiver unit 274 receives power signals from BTE 234, implantable stimulation module 244 or an additional external charging device. In such embodiments, power source 280 is configured to store power received by receiver unit 274, and to distribute power, as needed, to the elements of external stimulation module 250.

As noted, in certain embodiments of the present invention a rechargeable battery is included in external stimulation module 250. It would be appreciated that alternative power sources may also be used, including other bodily energy sources such as thermoelectric sources, vibration, or power continually or periodically emanated over a wireless power transfer link. In embodiments in which a continual or periodic power transfer link is implemented, external stimulation module 250 is configured to periodically verify that the wireless power transfer link is operational. If external stimulation module 250 determines that the power transfer link is non-operational or absent, the stimulation module automatically enters a power save mode of reduced power consumption.

In certain embodiments, external stimulation module 250 may further comprise one or more controls that provide a recipient or other user with the ability to control or alter the operation of external stimulation module 250. For ease of illustration, such controls are not shown in FIG. 2B.

The embodiments of FIG. 2B has been described with reference to a receiver unit 274 in external stimulation module 250. It should be appreciated that in alternative embodiments of the present invention external stimulation module may also comprises a transmitter unit to wirelessly transmit data signals to BTE 234 and/or implantable stimulation module 244. Alternatively, external stimulation module 250 may comprise a transceiver unit that is similar to the transceiver units described above.

As noted above, FIG. 2A illustrates embodiments of the present invention in which a multimodal auditory prosthesis comprises a BTE unit 234, an implantable stimulation module 244, and an external stimulation module 250. FIG. 3A is a schematic diagram of a multimodal auditory prosthesis 300 in accordance with embodiments of FIG. 2A In the embodiments of FIG. 3A, implantable stimulation module 244 is configured to be implanted beneath the recipient's skin/tissue 352. Implantable stimulation module 244 comprises internal transceiver unit 262, power source 212, stimulator unit 214 and electrode assembly 248 all implemented as described above with reference to FIG. 2A. Internal transceiver unit 262 comprises a coil 364 which functions as an antenna to inductively receive power and data from BTE 234.

As shown in FIG. 3A, BTE unit 234 has disposed therein or thereon one or more sound input elements, shown as microphone 324, for detecting sound. Microphone 324 converts the detected sound into electrical signals. Disposed in BTE unit 234 is a sound processing unit 322 that converts the microphone output into electrical signals. These electrical signals are provided to an external transceiver unit 310 disposed in BTE 234. External transceiver unit 310 comprises an antenna (not shown) and one or more circuit components (also not shown) which utilize the antenna to wirelessly transmit data signals representative of the output signal to implantable stimulation module 244. As noted, internal transceiver unit 262 comprises a magnetic induction coil 364 for receiving data signals from BTE 234. Therefore, in the exemplary arrangement of FIG. 3A, the antenna in external transceiver unit 310 also comprises a magnetic induction coil to provide wireless communication link 203.

As noted above, in certain embodiments BTE 234 is configured to provide power to implantable stimulation module 244. In such embodiments, BTE 234 comprises a power transmission module (not shown) connected to a magnetic induction coil 396 by a cable 398. The power transmission module is configured to utilize coil 396 to transmit power signals provided by power source 312 to coil 364 of internal transceiver unit 262 via a closely coupled induction link 317. Power source 312 is also used to provide power to the other components of BTE 234.

As shown, BTE 234 further comprises a user interface 334 that provides a recipient or other user with the ability to control or alter the functionality of BTE 234 or other components of prosthesis 300. User interface 334 may comprise, for example, a display screen and one or more input buttons. It would be appreciated that a variety of different user interfaces may be implemented.

As noted, auditory prosthesis 300 also comprises external stimulation module 250 configured to be non-surgically positioned in an externally accessible portion of the recipient's ear. In the embodiments of FIG. 3A, external stimulation module 250 comprises receiver unit 274, power source 280 and acoustic output transducer 282 all implemented as described above with reference to FIG. 2B. For ease of illustration, post-processing module 283 has been omitted.

As described above, receiver unit 274 is configured to wirelessly receive data signals from BTE 234 and/or implantable stimulation module 244 via links 205 and 201, respectively. In specific embodiments of the present invention, data signals representative of the output of sound processing unit 322 are provided to both implantable stimulation module 244 and external stimulation module unit 250. In such embodiments, stimulator unit 214 generates and delivers electrical stimulation signals to the recipient via electrode assembly 248 to evoke perception of a first frequency range of the sound detected at microphone 324. Concurrently, acoustic output transducer 282 uses the data signals wirelessly delivered to external stimulation module 250 to generate acoustic stimulation signals 310 that are delivered to the recipient to evoke a hearing perception of a second frequency range of the sound detected at microphone 324.

As noted, in the exemplary embodiments of FIG. 3A, stimulator unit 214 and electrode assembly 248 generate and deliver, respectively, electrical stimulation signals to the recipient's cochlea. The electrical stimulation signals evoke a hearing percept of a first frequency range of the sound detected at microphone 324. Although FIG. 3A illustrates the specific use of electrical stimulation, as noted elsewhere herein, implantable stimulation module 244 may be configured to deliver other types of stimulation the recipient's cochlea. For example, in certain embodiments, stimulation module 244 may comprise an auditory brain stimulator. In other embodiments, stimulation module 244 is configured to mechanically actuate the recipient's middle ear bones. In still other embodiments, stimulation module 244 has one or more components abutting the recipient's inner ear so as to directly generate (i.e. without requiring use of the middle ear bones) motion of the inner ear fluid.

As noted above, power source 280 may comprise a rechargeable power source. In certain embodiments, receiver unit 274 is configured to wirelessly receive power signals that are used to recharge power source 280. These wireless power signals may be provided by BTE unit 234 via link 205 or an additional link between coil 396 and receiver unit 234. In alternative embodiments, power signals are provided by implantable stimulation module 244 via link 201, or by an additional external device. For example, an additional external device may be provided that, when brought into proximity to external stimulation module 250, transmits power signals to receiver unit 274. It would be appreciated that a similar arrangement may be used to recharge power source 312 in BTE 234.

As noted several wireless communication links are provided to transmit power and data between the components of prosthesis 300. In certain embodiments, a time division multiple access (TDMA) scheme is implemented to transmit power/data via the different links. In other embodiments, an interleaving scheme as described in commonly owned and co-pending U.S. patent application Ser. No. 12/391,029, filed Feb. 23, 2009 may be implemented. The content of this application is hereby incorporated by reference herein.

FIG. 3B is a schematic diagram of a multimodal auditory prosthesis 302 in accordance with embodiments of the present invention. In the embodiments of FIG. 3B, implantable stimulation module 244 comprises internal transceiver unit 262, power source 212, stimulator unit 214 and electrode assembly 248 all implemented as described above with reference to FIG. 2A. Internal transceiver unit 262 comprises a coil 364 which functions as an antenna to inductively receive power and data from, for example, an external device. As shown in FIG. 3B, implantable stimulation module 244 further comprises an implantable microphone 390 configured to detect a sound. The use of implantable microphones to detect sounds is known in the art and will not be described further herein.

The output of microphone 390 is provided to a sound processing unit 352 disposed in implantable stimulation module 244. Sound processing unit 352 coverts the output to electrical signals usable by stimulator unit 214 to stimulate the recipient's ear. As noted, in the exemplary embodiments of FIG. 3B, stimulator unit 214 and electrode assembly 248 generate and deliver, respectively, electrical stimulation signals to the recipient's cochlea. The electrical stimulation signals evoke a hearing percept of a first frequency range of the sound detected at microphone 390. Although FIG. 3B illustrates the specific use of electrical stimulation, as noted elsewhere herein, implantable stimulation module 244 may be configured to deliver other types of stimulation the recipient's cochlea. For example, in certain embodiments, stimulation module 244 may comprise an auditory brain stimulator. In other embodiments, stimulation module 244 is configured to mechanically actuate the recipient's middle ear bones. In still other embodiments, stimulation module 244 has one or more components abutting the recipient's inner ear so as to directly generate (i.e. without requiring use of the middle ear bones) motion of the inner ear fluid.

Auditory prosthesis 302 also comprises external stimulation module 250 configured to be non-surgically positioned in an externally accessible portion of the recipient's ear. As such, external stimulation module 250 is separated from implantable stimulation module 244 by skin/tissue 352. In the embodiments of FIG. 3B, external stimulation module 250 comprises receiver unit 274, power source 280 and acoustic output transducer 282 all implemented as described above with reference to FIG. 2B. For ease of illustration, post-processing module 283 has been omitted.

During operation of prosthesis 302, internal transceiver unit 262 is configured to wirelessly transmit data signals representative of the output of sound processing unit 352 to receiver unit 274 via link 201. These data signals are utilized by acoustic output transducer 282 to generate acoustic stimulation signals 310 that are delivered to the recipient to evoke a hearing perception of a second frequency range of the sound detected at microphone 390. In certain embodiments of the present invention, the data signals are provided to external stimulation module 250 such that acoustic stimulation signals 310 and the electrical stimulation signals are delivered concurrently to the recipient.

As noted above, power source 280 may comprise a rechargeable power source. In certain embodiments, receiver unit 274 is configured to wirelessly receive power signals that are used to recharge power source 280. These wireless power signals may be provided by an additional external device that, when brought into proximity to external stimulation module 250, transmits power signals to receiver unit 274. For example, a BTE unit may be provided to charge power source 280. It would be appreciated that a similar arrangement may be used to recharge power source 212.

As noted several wireless communication links are provided to transmit power and data between the components of prosthesis 302. In certain embodiments, a time division multiple access (TDMA) scheme is implemented to transmit power/data via the different links. In other embodiments, an interleaving scheme as described in commonly owned and co-pending U.S. patent application Ser. No. 12/391,029 may be implemented.

FIG. 3C is a schematic diagram of a multimodal bilateral auditory prosthesis 304 in accordance with embodiments of the present invention. In the embodiments of FIG. 3C, implantable stimulation module 244 that is configured to be implanted beneath a recipient's skin/tissue 352. Implantable stimulation module 244 comprises internal transceiver unit 262, power source 212, stimulator unit and electrode assembly 248 all implemented as described above with reference to FIG. 2A. Internal transceiver unit 262 comprises a coil 364 which functions as an antenna to inductively receive power and data from, for example, an external device. Similar to the embodiments described above with reference to FIG. 3B, implantable stimulation module 244 further comprises an implantable microphone 390 configured to detect a sound, and configured to convert the detected sound into electrical signals.

The output of microphone 390 is provided to a sound processing unit 352 disposed in implantable stimulation module 244. Sound processing unit 352 coverts microphone output into electrical signals usable by stimulator unit 214 to stimulate the recipient's ear. As noted, in the exemplary embodiments of FIG. 3C, stimulator unit 214 and electrode assembly 248 generate and deliver, respectively, electrical stimulation signals to the recipient's cochlea. The electrical stimulation signals evoke a hearing percept of a first frequency range of the sound detected at microphone 390. Although FIG. 3C illustrates the specific use of electrical stimulation, as noted elsewhere herein, implantable stimulation module 244 may be configured to deliver other types of stimulation the recipient's cochlea. For example, in certain embodiments, stimulation module 244 may comprise an auditory brain stimulator. In other embodiments, stimulation module 244 is configured to mechanically actuate the recipient's middle ear bones. In still other embodiments, stimulation module 244 has one or more components abutting the recipient's inner ear so as to directly generate (i.e. without requiring use of the middle ear bones) motion of the inner ear fluid.

Bilateral auditory prosthesis 304 also comprises an external stimulation module 250A configured to be non-surgically positioned in an externally accessible portion of the recipient's first ear. As such, external stimulation module 250A is separated from implantable stimulation module 244 by skin/tissue 352A. In these embodiments, skin/tissue 352A comprises the tissue between the implanted location of implantable stimulation module 244 and the externally accessible portion of the recipient's first ear. As shown, external stimulation module 250A comprises receiver unit 274A, power source 280A and acoustic output transducer 282A all implemented as described above with reference to FIG. 2B. For ease of illustration, post-processing module 283 has been omitted.

In the illustrative embodiments of FIG. 3C, bilateral auditory prosthesis 304 further comprises an external stimulation module 250B configured to be non-surgically positioned in an externally accessible portion of the recipient's second ear. As such, external stimulation module 250B is separated from implantable stimulation module 244 by skin/tissue 352B. In these embodiments, skin/tissue 352B comprises the majority of the recipient's skull. As shown, external stimulation module 250B comprises receiver unit 274B, power source 280B and acoustic output transducer 282B all implemented as described above with reference to FIG. 2B. For ease of illustration, post-processing module 283 has been omitted.

During operation of bilateral prosthesis 304, internal transceiver unit 262 is configured to wirelessly transmit the electrical signals representing the sound processed data to receiver units 274 in external stimulation modules 250A and 250B via links 201A and 201B, respectively. These data signals are utilized by acoustic output transducers 282 to generate acoustic stimulation signals 310 that are delivered to the recipient's first and second ears to evoke a hearing perception of a frequency range of the sound detected at microphone 390. In certain embodiments of the present invention, the data signals are provided to external stimulation modules 250 such that acoustic stimulation signals 310 and the electrical stimulation signals are delivered concurrently to the recipient.

As noted, in the embodiments of FIG. 3C two communication links 201A and 201B are provided to transmit data between implantable stimulation module 244 and external stimulation modules 250. In certain embodiments, a time division multiple access (TDMA) scheme is implemented to transmit power via links 201.

FIG. 3C illustrates specific embodiments in which implantable stimulation module 244 transmits data signals to both external stimulation modules 250. In alternative embodiments of the present invention, one or both external stimulation modules 250 may transmit data signals to implantable stimulation module 244. FIG. 3D illustrates one such exemplary bilateral auditory prosthesis 306.

As shown in FIG. 3D, auditory prosthesis 306 comprises an implantable stimulation module 244 and an external stimulation module 250. Implantable stimulation module 244 comprises internal transceiver unit 262, power source 212, stimulator unit and electrode assembly 248 all implemented as described above with reference to FIG. 2A. Implantable stimulation module 244 further comprises a sound processing unit 423.

As shown, auditory prosthesis 306 also comprises an in-the-ear (ITE) device 350. ITE device 350 includes a microphone 378 to detect a sound, a power source 380, and a transmitter unit 376. During operation, the output of microphone 378 is wirelessly transmitted to sound processing unit 324 disposed in implantable stimulation module 244 via wireless communication link 319. Sound processing unit 324 coverts the microphone output into electrical signals usable by stimulator unit 214 to stimulate the recipient's ear. As noted, in the exemplary embodiments of FIG. 3D, stimulator unit 214 and electrode assembly 248 generate and deliver, respectively, electrical stimulation signals to the recipient's cochlea. The electrical stimulation signals evoke a hearing percept of a first frequency range of the sound detected at microphone 390. Although FIG. 3D illustrates the specific use of electrical stimulation, as noted elsewhere herein, implantable stimulation module 244 may be configured to deliver other types of stimulation the recipient's cochlea. For example, in certain embodiments, stimulation module 244 may comprise an auditory brain stimulator. In other embodiments, stimulation module 244 is configured to mechanically actuate the recipient's middle ear bones. In still other embodiments, stimulation module 244 has one or more components abutting the recipient's inner ear so as to directly generate (i.e. without requiring use of the middle ear bones) motion of the inner ear fluid.

As noted, bilateral auditory prosthesis 306 also comprises external stimulation module 250 configured to be non-surgically positioned in an externally accessible portion of the recipient's first ear. As shown, external stimulation module 250 comprises receiver unit 274, power source 280 and acoustic output transducer 282 all implemented as described above with reference to FIG. 2B. For ease of illustration, post-processing module 283 has been omitted.

In the illustrative embodiments of FIG. 3D, bilateral auditory prosthesis 304 further comprises an external stimulation module 250B configured to be non-surgically positioned in an externally accessible portion of the recipient's second ear. As shown, external stimulation module 250 comprises receiver unit 274, power source 280 and acoustic output transducer 282 all implemented as described above with reference to FIG. 2B. For ease of illustration, post-processing module 283 has been omitted.

During operation of bilateral prosthesis 306, internal transceiver unit 262 is configured to wirelessly transmit the electrical signals representing the sound processed data to receiver unit 274 in external stimulation module 250 via link 201. These data signals are utilized by acoustic output transducer 282 to generate acoustic stimulation signals 310.

In alternative embodiments of FIG. 3D, ITE device 350 may also comprises a sound processing unit. In such embodiments, data signals representing the speech processor output may be provided to implantable stimulation module 244 and/or external stimulation module 250.

FIGS. 3A-3C illustrate several exemplary variations of an auditory prosthesis in accordance with embodiments of the present invention. It should be appreciated that the illustrated embodiments may be combined to implement a number of different variations which have not been described in detail herein. These variations are within the scope of the present invention.

As noted above, an external stimulation module in accordance with embodiments of the present invention may be configured to deliver acoustic or mechanical energy to a recipient. Mechanical energy may be delivered via the physical coupling of a transducer to the tympanic membrane, the skull, the ossicular chain, the round or oval window or any other structure suitable to provide the imposed mechanical energy to the hydro-mechanical system in the inner ear. This type of energy delivery is referred to herein as mechanical stimulation. FIG. 4A is a perspective view of an external stimulation module in accordance with embodiments of the present invention configured to deliver mechanical stimulation via vibration of the bones and tissue surrounding a recipient's ear canal. Vibration of the bones of surrounding the recipient's ear canal causes motion of the recipient's inner ear fluid, thereby invoking a hearing percept, via bone conduction.

In the embodiments of FIG. 4A, external stimulation module 450 comprises a non-occluding in-the-canal vibrating component 402, and a retainer/component module 412.

Vibrating element 402 is configured to be implanted in the recipient's ear canal 102 (FIG. 1), and has a pass-through aperture 410 to permit the passage of bodily fluids and sound. Thus, vibrating component 402 is referred to herein as a non-occluding in-the-ear vibrating component.

The non-occluding aspect of vibrating component 402 avoids the occlusion effect (the wearer's own voice sounds altered to themselves because of closing the ear canal accentuates the low frequencies heard in the voice) commonly provided by conventional hearing aids. Other key advantages of having ear canal 410 open are that the recipient may hear ambient sounds making the recipient more aware of his/her environment.

Retainer/component module 412 is secured to the proximal end of vibrating component 402. Retainer/component module 412 is configured to be self-retained in the recipient's conchal bowl (not shown). In embodiments of FIG. 4A, retainer/component module 412 comprises the components described above with reference to FIG. 2B. Specifically, in the embodiments of FIG. 4A, retainer/component module 412 comprises a receiver unit that wirelessly receives data signals from one or more other components, such as, for example, a BTE unit or an implantable component. As described above, external stimulation module 450 is configured to generate vibration of the bone/tissue surrounding the ear canal based on these wirelessly transmitted data signals. Further details of a non-occluding vibrating component that may be implemented in embodiments of the present invention is described in commonly owned and co-pending International Patent Application No. PCT/US2007/074667, filed Jul. 27, 2007. The content of this application is hereby incorporated by reference herein.

FIG. 4B is a perspective view of an alternative external stimulation module 452 configured to deliver mechanical stimulation to a recipient in accordance with embodiments of the present invention. As shown in FIG. 4B, external stimulation module 452 comprises an in-the-canal vibrating component 424 having one or more vibrating extensions 422A and 422B (collectively referred to herein as vibrating extensions 422). Vibrating element 424 is configured to be implanted in ear canal 102 (FIG. 1), and comprises one or more spacers 426 to permit the passage of bodily fluids and sound. Thus, vibrating component 424 is referred to herein as an in-the-ear vibrating component.

External stimulation module 452 further comprises a retainer/component module 412 that is secured to the proximal end of vibrating component 424. Retainer/component module 412 is configured to be self-retained in the recipient's conchal bowl (not shown). In embodiments of FIG. 4B, retainer/component module 412 comprises the components described above with reference to FIG. 2B. Specifically, module 412 comprises a receiver unit that wirelessly receives data signals from one or more other components, such as, for example, a BTE unit or an implantable component. As described above, external stimulation module 452 is configured to generate vibration of the bone/tissue surrounding the ear canal based on these wirelessly transmitted data signals. Further details of an in-the-ear vibrating component that may be implemented in embodiments of the present invention is described in commonly owned and co-pending U.S. patent application Ser. No. 12/168,603, filed Jul. 7, 2008. The content of this application is hereby incorporated by reference herein.

All documents, patents, journal articles and other materials cited in the present application are hereby incorporated by reference.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An auditory prosthesis comprising:
    a sound processing unit configured to process sound and to generate electrical signals representing different frequency components of the processed sound;
    an implantable stimulation module communicably coupled to the sound processing unit, the stimulation module configured to stimulate a recipient to evoke a hearing percept of a first range of the frequency components; and
    an external stimulation module, configured to be positioned within an externally accessible portion of an ear of the recipient, comprising: a receiver unit configured to wirelessly receive the electrical signals representing the different frequency components, and a transducer configured to deliver acoustic or mechanical energy to the recipient's ear to evoke a hearing percept of a second range of the frequency components, wherein the second range of frequency components is different than the first range of frequency components.

2. The auditory prosthesis of claim 1, wherein the sound processing unit is disposed in the implantable stimulation module, and wherein the implantable stimulation module further comprises:
    an internal transceiver unit configured to transmit the electrical signals representing the different frequency components to the receiver unit in the external stimulation module.

3. The auditory prosthesis of claim 2, wherein the implantable stimulation module further comprises a rechargeable power source, and wherein the internal transceiver unit is configured to transcutaneously receive power signals from an external device for recharging the power source.

4. The auditory prosthesis of claim 1, wherein the sound processing unit is positioned in a behind-the-ear (BTE) unit, and wherein the BTE unit further comprises:
    an external transceiver unit configured to transmit the electrical signals representing the different frequency components to the receiver unit in the external stimulation module.

5. The auditory prosthesis of claim 4, wherein the stimulation module further comprises a transceiver unit, and wherein the external transceiver unit is configured to wirelessly transmit the electrical signals representing different frequency components to the transceiver unit in the stimulation module.

6. The auditory prosthesis of claim 4, wherein the external transceiver unit in the BTE is configured to transmit electrical signals representing a full range of the different frequency components of the processed sound to the receiver unit in the external stimulation module.

7. The auditory prosthesis of claim 6, wherein the receiver unit in the external stimulation module is configured to not be responsive to specific frequency components.

8. The auditory prosthesis of claim 6, wherein the stimulation module is configured to not be responsive to specific frequency components.

9. The auditory prosthesis of claim 4, wherein the external transceiver unit in the BTE is configured to transmit electrical signals representing a full range of the different frequency components of the processed sound to the stimulation module.

10. The auditory prosthesis of claim 1, wherein the external stimulation module further comprises a rechargeable power source.

11. The auditory prosthesis of claim 10, where the receiver unit is configured to wirelessly receive power signals for recharging the power source.

12. The auditory prosthesis of claim 1, wherein the sound processing unit is in a body worn unit, and wherein the body worn unit further comprises:
an external transceiver unit configured to transmit the electrical signals representing the different frequency components to the receiver unit in the external stimulation module.

13. The auditory prosthesis of claim 1, wherein the external stimulation module further comprises a transmitter unit.

14. The auditory prosthesis of claim 1, wherein the implantable stimulation module is configured to electrically stimulate the recipient's cochlea to evoke a hearing percept.

15. The auditory prosthesis of claim 1, wherein the stimulation module is configured to vibrate the recipient's skull to generate motion of the recipient's inner ear fluid via bone conduction.

16. The auditory prosthesis of claim 1, wherein the stimulation module is configured to actuate one or more of the recipient's middle ear bones to generate motion of the recipient's inner ear fluid.

17. The auditory prosthesis of claim 1, wherein the implantable stimulation module further comprises a component configured to be positioned adjacent to an opening in the cochlea configured to generate more direct motion of the recipient's inner ear fluid.

18. The auditory prosthesis of claim 1, wherein the transducer comprises a vibrating component configured to generate vibration of the recipient's skull to evoke a hearing percept via bone conduction.

19. The auditory prosthesis of claim 1, further comprising:
a second external stimulation module, configured to be positioned within an externally accessible portion of the recipient's second ear, comprising: a receiver unit to wirelessly receive the electrical signals representing different frequency components, and a transducer that delivers acoustic or mechanical energy to the recipient's second ear to evoke a hearing percept of a third range of the frequency components.

20. The auditory prosthesis of claim 1, wherein the prosthesis is configured to implement a time division multiple access (TDMA) scheme.

21. A bilateral auditory prosthesis comprising:
a sound processing unit configured to process sound and to generate electrical signals representing different frequency components of the processed sound;
an implantable stimulation module communicably coupled to the sound processing unit, the stimulation module configured to stimulate a recipient to evoke a hearing percept of a first range of the frequency components;
an external stimulation module, configured to be positioned within an externally accessible portion of a first ear of the recipient and comprising: a receiver unit configured to wirelessly receive the electrical signals representing the different frequency components, and a transducer configured to deliver acoustic or mechanical energy to the recipient's ear to evoke a hearing percept of a second range of the frequency components, wherein the second range of frequency components is different than the first range of frequency components; and
an external device, configured to be positioned within an externally accessible portion of the recipient's second ear, configured to wirelessly communicate with one or more of the stimulation module and the sound processing unit.

22. The auditory prosthesis of claim 21, wherein the external device comprises a sound input element to detect a sound, and a transmitter unit to provide an electrical representation of the detected sound to the sound processing unit.

23. The auditory prosthesis of claim 21, wherein the external device comprises a second external stimulation module, comprising: a receiver unit to wirelessly receive the electrical signals representing different frequency components, and a transducer that delivers acoustic or mechanical energy to the recipient's second ear to evoke a hearing percept of a range of the frequency components.

24. The auditory prosthesis of claim 21, wherein the sound processing unit is disposed in the implantable stimulation module, and wherein the implantable stimulation module further comprises:
an internal transceiver unit configured to transmit the electrical signals representing different frequency components to the receiver unit in the external stimulation module.

25. The auditory prosthesis of claim 24, wherein the implantable stimulation module further comprises a rechargeable power source, and wherein the internal transceiver unit is configured to transcutaneously receive power signals from an external device for recharging the power source.

26. The auditory prosthesis of claim 21, wherein the external stimulation module further comprises a rechargeable power source.

27. The auditory prosthesis of claim 26, where the receiver unit is configured to wirelessly receive power signals for recharging the power source.

28. The auditory prosthesis of claim 21, wherein the implantable stimulation module is configured to electrically stimulate the recipient's cochlea to evoke a hearing percept.

29. The auditory prosthesis of claim 21, wherein the stimulation module is configured to vibrate the recipient's skull to generate motion of the recipient's inner ear fluid via bone conduction.

30. The auditory prosthesis of claim 21, wherein the implantable stimulation module is configured to actuate one or more of the recipient's middle ear bones to generate motion of the recipient's inner ear fluid.

31. The auditory prosthesis of claim 21, wherein the implantable stimulation module further comprises a component configured to be positioned adjacent to an opening in the cochlea configured to generate more direct motion of the recipient's inner ear fluid.

32. The auditory prosthesis of claim 21, wherein the transducer comprises a vibrating component configured to generate vibration of the recipient's skull to evoke a hearing percept via bone conduction.

* * * * *